United States Patent [19]

Mills et al.

[11] Patent Number: 5,472,668

[45] Date of Patent: Dec. 5, 1995

[54] CARBON DIOXIDE MONITOR

[75] Inventors: Andrew Mills; Neil McMurray, both of Swansea, United Kingdom

[73] Assignee: Abbey Biosystems Limited, Swansea, United Kingdom

[21] Appl. No.: 853,753

[22] PCT Filed: Oct. 1, 1990

[86] PCT No.: PCT/GB90/01501

§ 371 Date: Feb. 9, 1992

§ 102(e) Date: Feb. 9, 1993

[87] PCT Pub. No.: WO91/05252

PCT Pub. Date: Apr. 18, 1991

[30] Foreign Application Priority Data

Sep. 29, 1989 [GB] United Kingdom ............... 8922049

[51] Int. Cl.[6] ............... A61M 16/00; H62B 9/06; G01N 17/00; G01N 31/22
[52] U.S. Cl. ............... 422/56; 422/57; 422/58; 422/85; 436/133; 436/169; 436/900; 128/719
[58] Field of Search ............... 436/133, 165, 436/169, 900; 422/55–60, 82.05, 84, 85, 88; 128/719; 424/7.1; 427/8

[56] References Cited

U.S. PATENT DOCUMENTS

| 4,418,037 | 11/1983 | Katsuyama | 422/56 |
| 4,495,291 | 1/1985 | Lawton | 436/1 |
| 5,124,129 | 6/1992 | Riccitelli et al. | 422/56 |

FOREIGN PATENT DOCUMENTS

| 0257916 | 3/1988 | European Pat. Off. | G01N 31/22 |
| 2624609 | 6/1989 | France | G01N 21/78 |
| WO8907957 | 9/1989 | WIPO | G01N 9/06 |
| WO9001695 | 2/1990 | WIPO | G01N 31/22 |

*Primary Examiner*—David A. Redding
*Attorney, Agent, or Firm*—Edwin D. Schindler

[57] ABSTRACT

The monitor which provides a detectable indication of the presence of an elevated proportion of carbon dioxide compared to that in normal ambient air, comprises a substrate coated by an intimate mixture of a transparent plasticised polymer vehicle, and an indicator material which undergoes a colour change on exposure to carbon dioxide. The indicator material comprises a salt of an indicator anion and a lipophilic organic quaternary cation. The device can be used to provide an indication of correct intubation of the trachea of a patient.

8 Claims, 3 Drawing Sheets

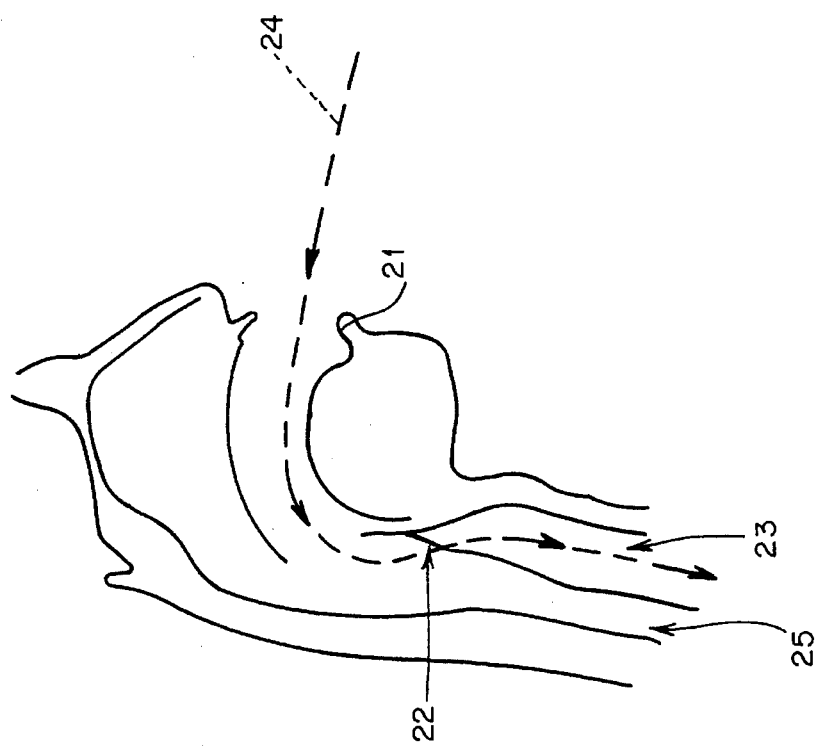
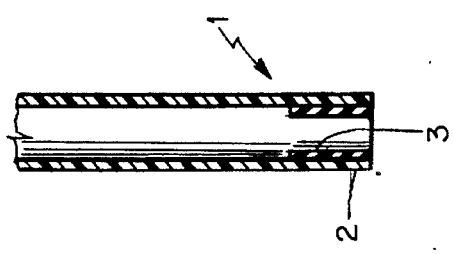

CO₂ Film Response, Temperature Dependence

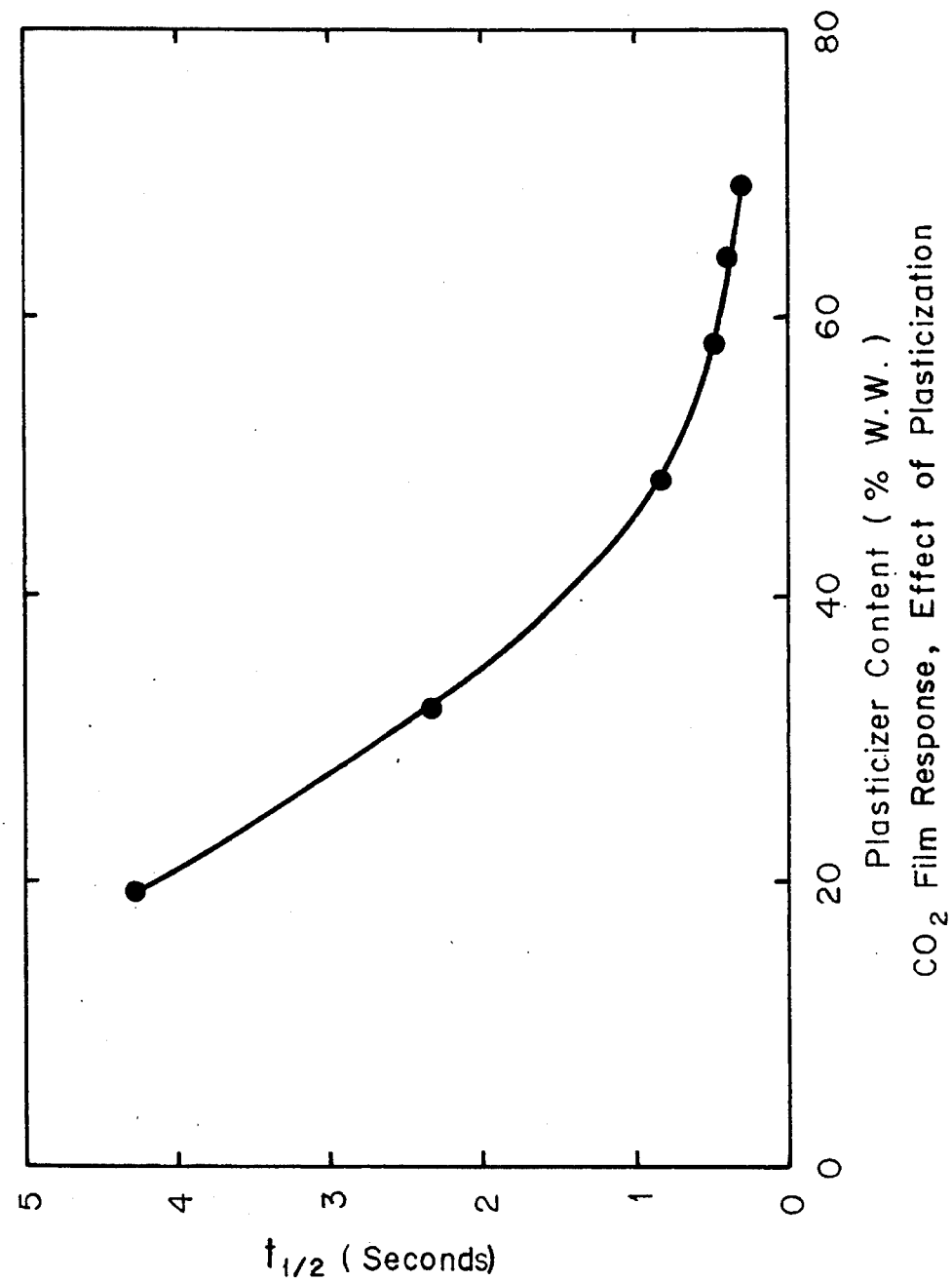

CARBON DIOXIDE MONITOR

BACKGROUND OF THE INVENTION

1. Technical Field of the Invention

The present invention is concerned with devices which provide a detectable indication that a volume of gas has an increased proportion of carbon dioxide compared to that present in normal ambient air. Such devices have a number of uses, one major use being to provide an indication of whether a tube has been correctly located in the airway (trachea) of a patient. There are many clinical situations where it is necessary to place a tube in the trachea of a patient. This is done in order to supply air or a mixture of oxygen and other gases to the lungs of the patient. The correct placement of the tube in the trachea is very important. Accidents have been reported where the tube has been inadvertently placed in the oesophagus. It has been observed that the air in the trachea contains about 6% carbon dioxide, whereas the oesophagus contains air in which the concentration of carbon dioxide is normal (about 0.03%).

2. Description of the Prior Art

Indicator devices which can detect the presence of an elevated proportion of carbon dioxide compared to that in air, and which can be used to determine whether a patient has been correctly intubated are described in U.S. Pat. No. 4728499, WO89/07957 and WO90/01695.

In all of these indicator devices, an indicator material is dispersed throughout a body of porous material: because the gas to be tested has to be passed through the body, the rate of flow is slow and therefore the response time is unacceptably long.

We have now devised an indicator device which has a rapid response, because of the manner in which the indicator material is provided.

SUMMARY OF THE INVENTION

According to the present invention, there is provided a carbon dioxide monitor which comprises a substrate having thereon an indicating film comprising an intimate mixture of a transparent film-forming polymer vehicle, a plasticiser therefor, an indicator material which undergoes a colour change on exposure to carbon dioxide, said indicator material being a salt of an indicator anion and a lipophilic organic quaternary cation.

The monitor according to the invention may, in some embodiments, be supplied in a sealed, gastight package, such as a pouch or sachet. Such a sachet may be formed from metallised polymer film, which is opaque in addition to being gas-impermeable.

When the monitor according to the invention is to be used to determine whether a patient has been correctly intubated, it is preferably provided in sterilised form in such a sealed package. In this embodiment of the invention, the monitor preferably consists of gamma-pay sterilisable materials.

During gamma ray sterilisation acidic moieties tend to be generated within the sensor films which may result in the film pH becoming too low to permit the effective indication of carbon dioxide (the indicator dye is permanently present in the acid form). This difficulty may be overcome simply by the incorporation of extra quantities of quaternary cation buffer salt. The latter neutralizes acid as it is generated within the film and keeps the film pH within acceptable limit.

The indicating film is preferably formulated such that no detectable colour change takes place on exposure to room air (ambient carbon dioxide 0.03%) for a prolonged period, while the response to carbon dioxide levels of 2 to % is rapid (generally about 1 to 2 seconds). The range 2 to % is of importance medically, because this corresponds to the concentration present in exhaled breath.

The colour change may be observed visually (in which case a qualitative indication of carbon dioxide concentration is obtained) or spectrophotometrically (when a quantitative indication of the carbon dioxide concentration may be obtained).

The transparent film-forming polymer vehicle should be compatible with the indicator material, such that the latter does not exude or otherwise undergo phase separation over a prolonged period; it should in addition be hydrolytically stable (as should the plasticiser) in order to avoid unwanted changes in the pH in the absence of carbon dioxide. The polymer should furthermore be permeable to carbon dioxide (this permeability being enhanced by the plasticiser).

The hydrolytically stable polymer may be water-soluble or organic solvent-soluble (the latter being preferred). Examples of suitable organic solvent soluble polymers include polyvinyl butyral, polyvinyl methyl ether, polymethyl methacrylate, ethyl cellulose and polystyrene.

Examples of water-soluble polymers with good resistance to hydrolysis include hydroxypropyl cellulose, methyl cellulose, carboxymethyl cellulose, polyethylene glycol, polyvinyl alcohol (100% hydrolysed) and polypropylene glycol.

The hydrolytically stable plasticiser may be water-soluble organic solvent-soluble (depending on the polymer vehicle).

Examples of suitable organic solvent-soluble plasticisers include alkyl triesters of phosphoric acid (including tributyl phosphate, triethyl phosphate and tris butoxyethyl phosphate), branched chain esters of carboxylic acids, especially those with secondary or tertiary alcohols (including diisopropyl phthalate and diethylhexyl sebacate), sulphamides (including p-toluene sulphonamide). Examples of water-soluble plasticisers with a good resistance to hydrolysis include alcohols (including glycerine and trimethylolpropane) and ethers (including low molecular weight polyethylene glycol).

The indicator is preferably one which undergoes a well-defined colour change on exposure to carbon dioxide (for example, it may undergo a blue to yellow colour change).

Examples of suitable indicator anions are azo dyes (including alpha-naphthol orange), nitrophenol dyes (including m-nitrophenol and p-nitrophenol), phthalein dyes (including alphanaphtholphthalein and o-cresolphthalein), sulphonephthalein dyes (including m-cresol purple, cresol red, thymol blue and alphanaphtholsulphonephthalein), triphenylmethane dyes (including rosolic acid) and indophenol dyes (including indophenol and 1-naphthol-2-sulphonic acid indophenol).

Examples of suitable quaternary cations are: ammonium cations (including benzyltrimethyl ammonium, trioctylmethyl ammonium, tricaprylmethyl ammonium, tetrabutyl ammonium, tetrahexyl ammonium and tetraoctyl ammonium) and phosphonium cation (including tetraphenyl phosphonium, trioctyl phosphonium and hexadecyl tributyl phosphonim). A preferred quaternary cation is tetrabutyl ammonium. The salts of quaternary cations (ammonium and phosphonium) become insoluble in water when the cation is above a certain molecular weight (approximately C24 in the case of symmetrical aliphatic quaternary ammoniums). This phenomenon may be exploited to confer enhanced water resistance on non-aqueous sensor films by rendering the dye and buffer components immune to dissolution and "wash out" by liquid water.

The salt of the indicator anion and the lipophilic quaternary cation may be produced simply by adding a stoichiometric amount of the quaternary hydroxide to the indicator in its free acid form.

The substrate should be such that it is free of mobile components capable of migrating into the indicating film: equally it should resist migration of components from the latter film. Furthermore, the substrate should be chemically inert relative to the film.

Suitable inorganic materials for use as the substrate include glasses, ceramics, and crystalline materials; suitable organic materials include paper, polyolefins (such as polypropylene or polyethylene) and fluorocarbons (such as PTFE). When polymers are used, they should be free of reactive or migratory plasticisers, lubricants, antioxidants or the like. The substrate may be in the form of a simple tube or plate; in one preferred embodiment the substrate is in the form of a connector or junction piece for a catheter. In another embodiment of the invention, the substrate may be in the form of a tube which is open at both ends; this may be used to monitor the carbon dioxide content of expired breath in a method in which the patient breaths through the tube and the colour change in the indicator film monitored. This method may be used for determination of the end-tidal carbon dioxide (that is, the carbon dioxide present in the final expiration of a deep, breath from the lungs). The carbon dioxide monitor according to the invention may be used for long term continuous monitoring of carbon dioxide concentration if acidifying and oxidising gases are removed from the air prior to contact with the film. This may be achieved using a "guard" or "scrubbing" device incorporating (i) the salt of an involatile acid with a pKa intermediate between carbonic acid and the polluting volatile acid (eg. sulphurous acid) and (ii) an antioxidant or antiozonant.

BRIEF DESCRIPTION OF THE DRAWING FIGURES

Reference will now be made to the accompanying drawings, in which:

FIG. 1 is a side elevation showing one form of monitor according to the invention:

FIG. 2 is a simplified and anatomical diagram showing how correct intubation of the trachea is effected;

FIG. 4 is a graphical representation of the effect of plasticisation on film response, in a film according to a further embodiment of the invention.

DETAILED DESCRIPTION OF THE DRAWING FIGURES

Figure 3:
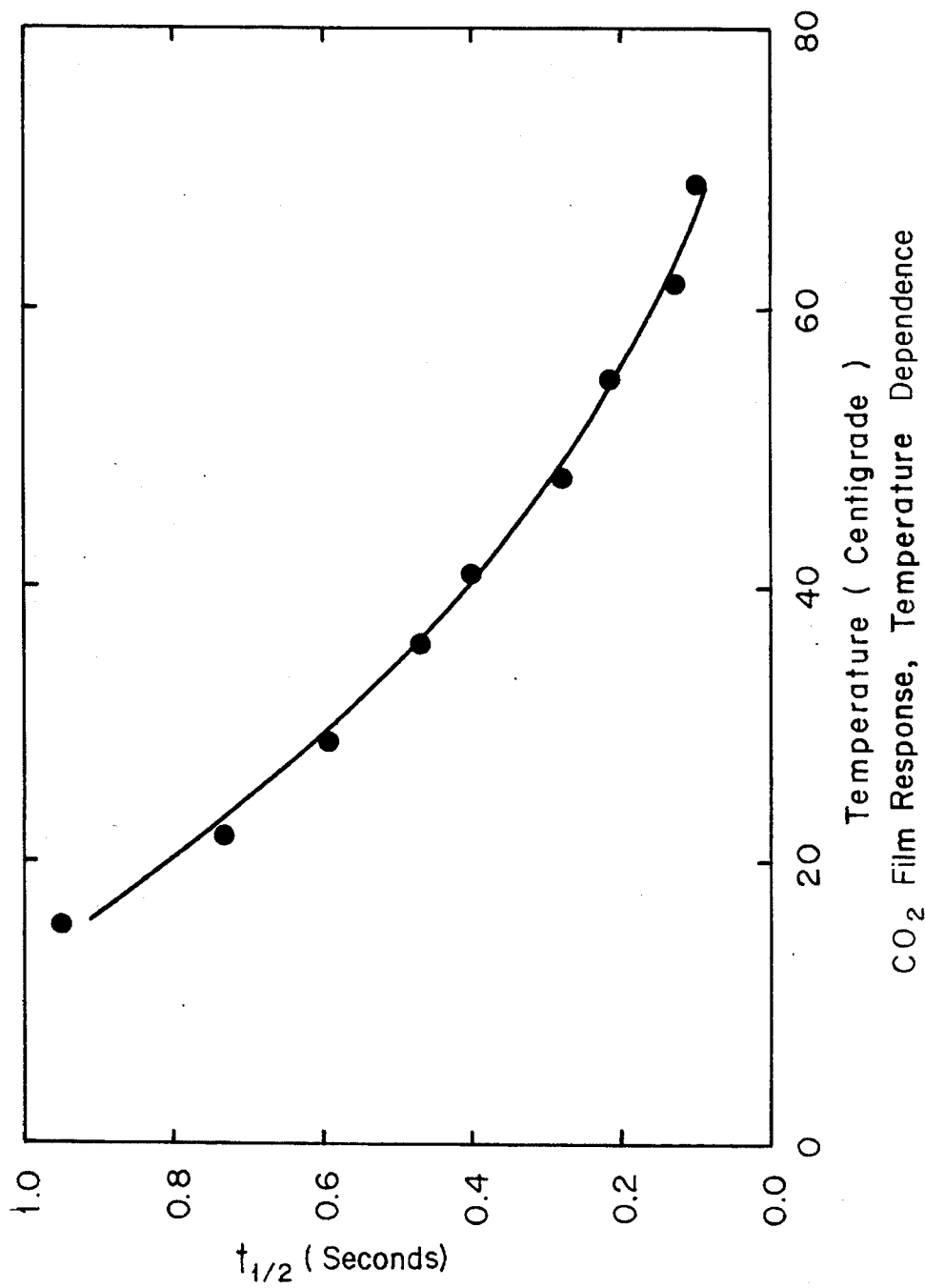
FIG. 3 is a graphical representation of the temperature dependance of an exemplary plasticised film formulated in a device according to the invention.

Referring to FIG. 1, there is shown a device comprising a relatively gas-impermeable tube 2; at one end 2 of tube 2 is an end cover 3 of a membrane which is of a material which is highly permeable to carbon dioxide (of a material such as a silicone rubber). The internal surface 3 of tube 1 is provided with a coating of indicator material as described above.

Referring to FIG. 2, a portion of a head and neck is shown; passing along the mouth 21, through the epiglottis 22 to the trachea 23 is a dotted line 24 showing the path of correct intubation. If the tracheal tube failed to pass through the epiglottis, it would pass down the oesophagus 25 in error.

If a device such as that illustrated in FIG. 1 were to be passed along the tracheal tube, when the leading edge thereof reaches the tracheal zone, the, device would respond to the higher carbon dioxide content by undergoing a change of detectable colour in the indicator layer. On the contrary, if the leading end of the device were to be located erroneously in the oesophagus, there would be no resulting colour change. This therefore provides a simple and effective test for whether or not a tracheal tube has been correctly inserted in the trachea.

The present invention has been described primarily with reference to a device for use in determining whether a patient has been correctly intubated; other uses of a monitor according to the invention are envisaged, such as for use as a personnel monitor for use in potentially hazardous environments, such as ships' holds, tanks or the like.

The following Examples illustrate the preparation of carbon dioxide monitors according to the invention.

EXAMPLE 1

(organosoluble film)
Formulation
  dye-quaternary cation/polymer-plasticiser/support
    m-cresol purple-tetrabutylammonium cation/ethyl cellulose-tri-n-butyl phosphate/glass
Preparation A solution (solution A) was prepared by adding 0.1 g of m-cresol purple in 0.66 g of 30% w/w tetrabutyl ammonium hydroxide in methanol. The resulting mixture was dissolved in sufficient extra methanol to give a solution which was 2% w/w with respect to the m-cresol purple. A second solution (solution B) was prepared by dissolving 10 g of ethyl cellulose (46% ethoxy content) in 90 g of a mixture of toluene and ethanol (88:20 by volume).

To 10 g of solution B were added 2 g of tri-n-butyl phosphate, 1 g of solution A and 0.085 g of 30.5% tetrabutyl ammonium hydroxide in methanol. The resulting solution was well mixed and cast through a 75 microns thick ten, plate. The solvent was allowed to evaporate at 30 degrees Celsius in air. The resulting film was ca. 20 microns thick.

EXAMPLE 2

(water soluble film)
Formulation
  dye-quaternary cation/polymer-plasticiser/support
  m-cresol purple-tetrabutylammonium cation/hydroxypropyl cellulose-Carbowax 600/glass
Preparation A solution (solution C) was prepared by dissolving 5 g of hydroxypropyl cellulose (mol. weight 30,000) in 100 cm$^3$ of distilled water. To 10 g of solution C was added: 1 g of Carbowax 600 (i.e. polyethylene glycol mol. weight 600), 0.5 g of solution A (as described in Example 1) and 0.045 g of 30.5% w/w tetrabutyl ammonium hydroxide in methanol. The resulting solution was cast through a 125 microns template and the solvent evaporated in an oven at 90 degrees Celsius for 2 min. The film thus obtained was ca. 17 microns thick.

EXAMPLE 3

(organo-soluble)
Formulation
  dye-quaternary cation/polymer-plasticiser/support
  thymol blue-tetrabutylammonium cation/polyvinyl butyral-tris(2, ethylhexyl) phosphate/glass
Preparation A solution (solution D) was prepared by adding 0.1 g of thymol blue to 0.66 g of 30% w/w tetrabutyl ammonium hydroxide in methanol. The resulting mixture was dissolved in sufficient extra methanol to give a 2% w,w solution with respect to thymol blue. A second solution (solution E) was prepared by dissolving 10 g of polyvinyl butyral (mol. weight 125,000) in 90 g of ethanol. To 10 g of solution E were added: 2 g of tris(2,ethylhexyl) phosphate, 1 g of solution D and 0.085 tg of 30.5% tetrabutyl ammonium hydroxide in methanol. The final solution was cast through a 75 microns thick template and the solvent allowed to evaporate in air. The resulting film was ca 20 microns thick.

EXAMPLE 4

(organosoluble)
Formulation
  dye-quaternary cation/polymer-plasticiser/support
  cresol red-tetrabutylammonium cation/polyvinyl butyrol-tris(2, ethylhexyl) phosphate/glass
Preparation A solution (solution F) was prepared by adding 0.1 g of cresol red to 0.66 g of 30.5% tetrabutyl ammonium hydroxide in methanol. The resulting mixture was dissolved in sufficient extra methanol to give a solution which was 2% w/w with respect to cresol red. To 10 g of solution E were added 2 g of this (2, ethyl-hexyl) phosphate, 1 g of solution F and 0.085 g of 30.5% w/w teterabutyl ammonium hydroxide in methanol. The final solution was cast through a 75 microns screen and the solvent allowed to evaporate in air at 30 degrees Celsius. The resulting film was ca 20 microns thick.

EXAMPLE 5

A solution (solution A) was prepared by the addition to 0.1 g cresol red of 4.05 g 10.9% w/w tetraoctyl ammonium hydroxide in methanol followed by the addition of sufficient extra methanol to cause the solution to be 2% W.W with respect to cresol red. A second solution (solution B) was prepared by dissolving 12 g of polyvinyl butyral (mol. wt. 125,000) in 88 g of ethanol. To 10 g of solution B were added 2.4 g of tris (2, ethylhexyl) phosphate and 1.2 g of solution A. The final solution was cast through a 75 micron template and the solvent allowed to evaporate in air. The resulting film was ca. 20 microns thick and was composed as follows:

| | |
|---|---|
| P.V.B | 32.2% w.w |
| tris E.H.P | 64.3% |
| tetra octyl ammonim | 2.6% |
| cresol red | 0.64% |

The film described above showed no tendency to lose either indicator dye or buffer capacity cansequent to exposure to liquid water over indefinite periods.

7. Film Characteristics 7.1 UV-Vis. Absorption Spectra

The UV-Visible absorption spectrum of each of the films was recorded in a nitrogen and a carbon dioxide atmosphere and table 1 gives the wavelength of the maximum peak in the two different environments:

TABLE 1

Absorption peaks in $N_2$ and $CO_2$

| Example | $CO_2$ max/nm (acidic form) | $N_2$ max/nm (alkaline form) | Observed Color Change ($N_2 \rightarrow CO_2$) |
|---|---|---|---|
| 1 | 427 | 605 | blue ---> yellow |
| 2 | 415 | 596 | blue ---> yellow |
| 3 | 414 | 613 | blue ---> yellow |
| 4 | 419 | 589 | purple ---> yellow |

7.2 Equilibrium Response to $CO_2$

The absorbance change exhibited by each film to different $CO_2$ concentrations was monitored at the of the $_{max}$ of the alkaline form of the indicator dye. The % response was defined as follows:

$$\% \text{ resoponse} = 100\{A_0 - A_x\}/A_0$$

where $A_0$ and $A_x$ are the absorbances of the dye when exposed to 0% and x% $CO_2$ respectively. Typical results for each of the Examples are given in the following table:

TABLE 2

Film % response for different % $CO_2$ levels

| | % response | | | |
|---|---|---|---|---|
| % $CO_2$ level: | 0.03% | 2% | 5% | 100% |
| Example | | | | |
| 1 | 10 | 80.7 | 89.2 | 97.3 |
| 2 | 8 | 75.0 | 85.7 | 98.3 |
| 3 | 11 | 85.2 | 92 | 99.6 |
| 4 | 2.3 | 32.2 | 49.6 | 88.3 |

As indicated by the results in table 2, upon exposure of the Example films 1, 2 and 3, from aid (0.03% $CO_2$) to 2% $CO_2$ the colour change is clear and dramatic and highly suited for a qualitative visual indication of exhaled breath.

7.3 Response Time Characteristics

Each film was exposed to a variety of step-wise changes in % $CO_2$ and the 50% and 90% response times were determined spectrometrically by monitoring the absorbance at the $_{max}$ for the alkaline form of the indicator dye. Typical results arising from this work are given in the following tables:

TABLE 3

50% response times

| | response time (s) | | | |
|---|---|---|---|---|
| % CO$_2$ change: | 0.03% -> 2% | 2% -> 0.03% | 0.03% -> 5% | 5% -> 0.03% |
| Example | | | | |
| 1 | 0.68 | 2.0 | 0.30 | 1.6 |
| 2 | 3.5 | 12.5 | 1.8 | 9.75 |
| 3 | 1.0 | 2.8 | 0.55 | 2.4 |
| 4 | — | — | 0.80 | 0.86 |

TABLE 4

90% response times.

| | response time (s) | | | |
|---|---|---|---|---|
| % CO$_2$ change: | 0.03% -> 2% | 2% -> 0.03% | 0.03% -> 5% | 5% -> 0.03% |
| Example | | | | |
| 1 | 1.83 | 10.4 | 0.76 | 6.6 |
| 2 | 10.5 | 50 | 5.2 | 69.3 |
| 3 | 2.6 | 27.2 | 1.25 | 18.6 |
| 4 | — | — | 1.92 | 1.60 |

From the results in tables 3 and 4 it is clear that response time is dependant upon film composition and that the response to rising % CO$_2$ can be very rapid (see example 1). It appears from this and other work that films 1,2 and 3 exhibit an assymetric response to rising and falling CO$_2$ levels. This may be viewed as advantageous in their application as qualitative, visual indicators of CO$_2$ in exhaled breath, since the colour change will be steadier and more persistant in the presence of the fluctuating CO$_2$ levels experienced in such determinations. Interestingly, Example film 4 gives an almost symmetric response to rising and falling % CO$_2$ levels and thus is more likely to find application in time-resolved qualitative analysis of varying levels of CO$_2$, as found in exhaled breath.

7.4 Temperature dependence

FIG. 3 shows the CO$_2$ response characteristics of the film at different temperatures. The figure is derived from measurements made on the film described in Example 5 (waterproof film 20 microns thick).

7.5 Plasticiser Content

FIG. 4 shows the effect of plasticisation on the CO$_2$ film response. The results were obtained by keeping the cresol red and tetraoctyl ammonium content of the film formulation constant at the values given for Example 5 (film thickness 20 microns) but varying the ratio of polymer:plasticiser.

We claim:

1. A carbon dioxide monitor, which comprises a substrate having thereon an indicating member comprising a transparent polymer vehicle mixed with an indicator material which undergoes a color change on exposure to carbon dioxide, the improvement comprises having said indicating member in the form of a film in which said indicator material comprises a salt of an indicator anion and a lipophilic organic quaternary cation.

2. The carbon dioxide monitor according to claim 1, wherein said substrate and said indicating member are gamma-ray sterilizable materials.

3. The carbon dioxide monitor according to claim 1, wherein said film is hydrolytically stable.

4. The carbon dioxide monitor according to claim 1, wherein said film iS permeable to carbon dioxide.

5. The carbon dioxide monitor according to claim 1, wherein said film is water-insoluble.

6. The carbon dioxide monitor according to claim 1, wherein said quaternary cation is a member selected from the group consisting of tetrabutyl ammonium or tetraoctyl ammonium.

7. The carbon dioxide monitor according to claim 1, wherein said film is plasticized.

8. The carbon dioxide monitor according to claim 1, wherein said substrate is in the form of a connector or junction piece for a catheter.

* * * * *